United States Patent
Scholl et al.

(10) Patent No.: US 10,406,054 B1
(45) Date of Patent: Sep. 10, 2019

(54) SYSTEMS AND METHODS FOR FACILITATING SURGICAL PROCEDURES

(71) Applicant: NuVasive, Inc., San Diego, CA (US)

(72) Inventors: Thomas Scholl, San Diego, CA (US); Eric Finley, San Diego, CA (US); Brian Snider, San Diego, CA (US); Amanda Bloom, San Diego, CA (US)

(73) Assignee: NuVasive, Inc., San Diego, CA (US)

(*) Notice: Subject to any disclaimer, the term of this patent is extended or adjusted under 35 U.S.C. 154(b) by 687 days.

(21) Appl. No.: 15/047,049

(22) Filed: Feb. 18, 2016

Related U.S. Application Data

(60) Provisional application No. 62/117,564, filed on Feb. 18, 2015.

(51) Int. Cl.
  *A61G 13/00* (2006.01)
  *A61G 13/08* (2006.01)
  *A61B 6/04* (2006.01)

(52) U.S. Cl.
  CPC .......... *A61G 13/08* (2013.01); *A61B 6/0407* (2013.01); *A61G 13/0036* (2013.01); *A61G 13/0054* (2016.11)

(58) Field of Classification Search
  CPC .............. A61G 7/008; A61G 13/0036; A61G 13/0054; A61G 13/0081; A61G 13/02; A61G 13/04; A61G 13/08; A61G 7/015; A61B 6/0407
  See application file for complete search history.

(56) References Cited

U.S. PATENT DOCUMENTS

| | | |
|---|---|---|
| 5,658,286 A | 8/1997 | Sava |
| 6,112,349 A * | 9/2000 | Connolly ............... A61G 7/001 5/430 |
| RE42,226 E | 3/2011 | Foley |
| 7,957,831 B2 | 6/2011 | Isaacs |
| 8,235,998 B2 | 8/2012 | Miller |
| 8,442,621 B2 | 5/2013 | Gorek |
| 8,744,826 B2 | 6/2014 | Skalli |
| 8,753,346 B2 | 6/2014 | Suarez |
| 8,831,324 B2 | 9/2014 | Penenberg |
| 8,983,813 B2 | 3/2015 | Miles |

(Continued)

FOREIGN PATENT DOCUMENTS

| | | |
|---|---|---|
| DE | 102011006574 | 10/2012 |
| WO | WO-2009035358 | 3/2009 |

(Continued)

OTHER PUBLICATIONS

Schlenk, Richard P., et al., "Biomechanics of Spinal Deformity"; Neurosurg Focus, 14(1): Article 2, Jan. 2003; vol. 14.

(Continued)

*Primary Examiner* — Nicholas F Polito

(57) ABSTRACT

The present subject disclosure provides a novel system and method of maintaining a patient in an optimal position for spinal or other surgeries where the position of the patient and access to the surgical site may be very helpful. Further, neurophysiological data is obtained from the patient in real time through sensors on the patient contacting platforms and relayed to a system which determines whether the patient position should be moved to maintain optimal and viability health during the procedure.

16 Claims, 2 Drawing Sheets

(56) References Cited

U.S. PATENT DOCUMENTS

| | | | |
|---|---|---|---|
| 8,992,542 B2 | 3/2015 | Hagag | |
| 9,119,670 B2 | 9/2015 | Yang | |
| 9,129,054 B2 | 9/2015 | Nawana | |
| 9,204,937 B2 | 12/2015 | Edelhauser | |
| 9,211,145 B2 | 12/2015 | Pereiro de Lamo | |
| 9,233,001 B2 | 1/2016 | Miles | |
| 9,248,002 B2 | 2/2016 | McCarthy | |
| 9,320,604 B2 | 4/2016 | Miles | |
| 9,408,698 B2 | 8/2016 | Miles | |
| 9,452,050 B2 | 9/2016 | Miles | |
| 9,572,682 B2 | 2/2017 | Aghazadeh | |
| 9,597,157 B2 | 3/2017 | Hagag | |
| 9,662,228 B2 | 5/2017 | McCarthy | |
| 9,700,292 B2 | 7/2017 | Nawana | |
| 9,724,167 B2 | 8/2017 | Ziaei | |
| 2002/0138905 A1* | 10/2002 | Bartlett | A61G 7/001 5/607 |
| 2004/0133983 A1* | 7/2004 | Newkirk | A61G 13/0036 5/624 |
| 2007/0073137 A1 | 3/2007 | Schoenefeld | |
| 2011/0099716 A1* | 5/2011 | Jackson | A61G 13/0036 5/607 |
| 2012/0035507 A1 | 2/2012 | George | |
| 2013/0053854 A1 | 2/2013 | Schoenefeld | |
| 2013/0198958 A1* | 8/2013 | Jackson | A61G 13/0036 5/607 |
| 2013/0345757 A1 | 12/2013 | Stad | |
| 2014/0076883 A1 | 3/2014 | Brailovski | |
| 2014/0081659 A1 | 3/2014 | Nawana | |
| 2014/0378828 A1 | 12/2014 | Penenberg | |
| 2015/0073265 A1 | 3/2015 | Popovic | |
| 2015/0157416 A1 | 6/2015 | Andersson | |
| 2015/0164721 A1* | 6/2015 | Miyashita | A61G 7/0573 5/617 |
| 2015/0227679 A1 | 8/2015 | Kamer | |
| 2015/0238271 A1 | 8/2015 | Wollowick | |
| 2015/0282796 A1 | 10/2015 | Nawana | |
| 2016/0000621 A1* | 1/2016 | Jackson | A61G 13/06 5/618 |

FOREIGN PATENT DOCUMENTS

| | | |
|---|---|---|
| WO | WO-2013085982 | 6/2013 |
| WO | WO-2014016824 | 1/2014 |
| WO | WO-2014088801 | 6/2014 |

OTHER PUBLICATIONS

Smith, et al., "Clinical and Radiographic Evaluation of the Adult Spinal Deformity Patient"; Neurosurg Clin N An 24 (2), 143-156; Feb. 21, 2013.

Tanquay, et al., "Clinical and Radiographic Evaluation of the Adult Spinal Deformity Patient"; Neurosurg Clin N An 24 (2), 143-156; Feb. 21, 2013.

Lehman, et al., "Do Intraoperative Radiographs in Scoliosis Surgery Reflect Radiographic Result?"; Clin Orthop Relat Res (2010) 468: 679-686.

Spine: Patient Positioning Solutions, https://www.allenmedical.com/files/resources/us_spine_brochure.pdf.

* cited by examiner

SYSTEMS AND METHODS FOR FACILITATING SURGICAL PROCEDURES

This application claims priority to U.S. Provisional Patent Application Ser. No. 62/117,564, filed on Feb. 18, 2015, the contents which are hereby incorporated by reference herein in their entirety into this disclosure.

TECHNICAL FIELD

The subject disclosure relates generally to patient positioning techniques. Specifically, the subject disclosure relates to patient positioning systems and methods of use in the field of surgery, and more particularly spine surgery.

BACKGROUND OF THE SUBJECT DISCLOSURE

Back problems are one of the most common and debilitating ailments, afflicting people from all walks of life. In the United States alone, over 500,000 spine lumbar and cervical fusion procedures are performed each year. One of the causes of back pain and disability results from the rupture or degeneration of one or more intervertebral discs in the spine. Surgical procedures are commonly performed to correct problems with displaced, damaged, or degenerated intervertebral discs due to trauma, disease, or aging. Generally, spinal fusion procedures involve removing some or the all of the diseased or damaged disc, and inserting one or more intervertebral implants into the resulting disc space. Anterior lumbar interbody fusion (ALIF), posterior lumbar interbody fusion (PLIF and TLIF) and lateral lumbar interbody fusion (for example, XLIF®) procedures are some of the techniques that spine surgeons use to access the portions of the spine to be repaired or replaced. In some instances, it may be necessary to utilize more than one technique in order to achieve full surgical correction. Access to the spine using these and other techniques involves proper patient positioning on an operating table. The table and its ability to facilitate positioning the patient in one or more desired anatomical positions may be useful in assisting the surgeon in more fully addressing the scope of the patient's ailment.

SUMMARY OF THE SUBJECT DISCLOSURE

The present subject disclosure provides a novel system and method of maintaining a position in an optimal position for spinal or other surgeries where the position of the patient and access to the surgical site may be very helpful.

In one exemplary embodiment, the subject matter is a system for maintaining a patient in a desired position. The system includes a first end member having an open interior portion, and a first crossing member attached to the interior portion of the first end member; a second end member having an open interior portion, and a second crossing member attached to the interior portion of the second end member; a base connecting the first and second end members; a first substantially flat platform connected to the first crossing member; a second substantially flat platform connected to the second crossing member; wherein the first and second platforms are independently movable in three dimensions and may be lined up to form a single continuous substantially planar surface.

In another exemplary embodiment, the subject matter is a system for maintaining a patient in a desired position. The system includes a first end member having an open interior portion, and a first crossing member attached to the interior portion of the first end member; a second end member having an open interior portion, and a second crossing member attached to the interior portion of the second end member; a base connecting the first and second end members; a first substantially flat platform connected to the first crossing member; a second substantially flat platform connected to the second crossing member; sensors within the first and second platforms adapted to read signals thereon and generate signals; and a position monitoring system adapted to receive the signals from the sensors and determine a physiological condition of the patient; wherein the first and second platforms are independently movable in three dimensions and may be lined up to form a single continuous substantially planar surface.

In yet another exemplary embodiment, the subject matter is a method for maintain a patient in a desired position. The method includes providing a bed system having independently moving upper and lower platforms having sensors therein, wherein the lower portion further comprises a pivoting distal portion; positioning the patient on the upper and lower platforms such that the upper portion supports a portion of the patient from a waist portion and higher, and the bottom portion supports a portion of the patient from the waist portion and lower, wherein the pivoting portion is relatively positioned between the waist portion and a pelvic region; measuring neurological data from the portions of the patient body in contact with the sensors; relaying the neurophysiological data to a neurophysiological monitoring system; adjusting the position of the patient with respect to the upper and lower platforms upon determining that the neurophysiological data requires moving of the patient to ensure optimal patient health.

BRIEF DESCRIPTION OF THE DRAWINGS

Many advantages of the present subject disclosure will be apparent to those skilled in the art with a reading of this specification in conjunction with the attached drawings, which include.

DETAILED DESCRIPTION OF THE SUBJECT DISCLOSURE

Figure 1:
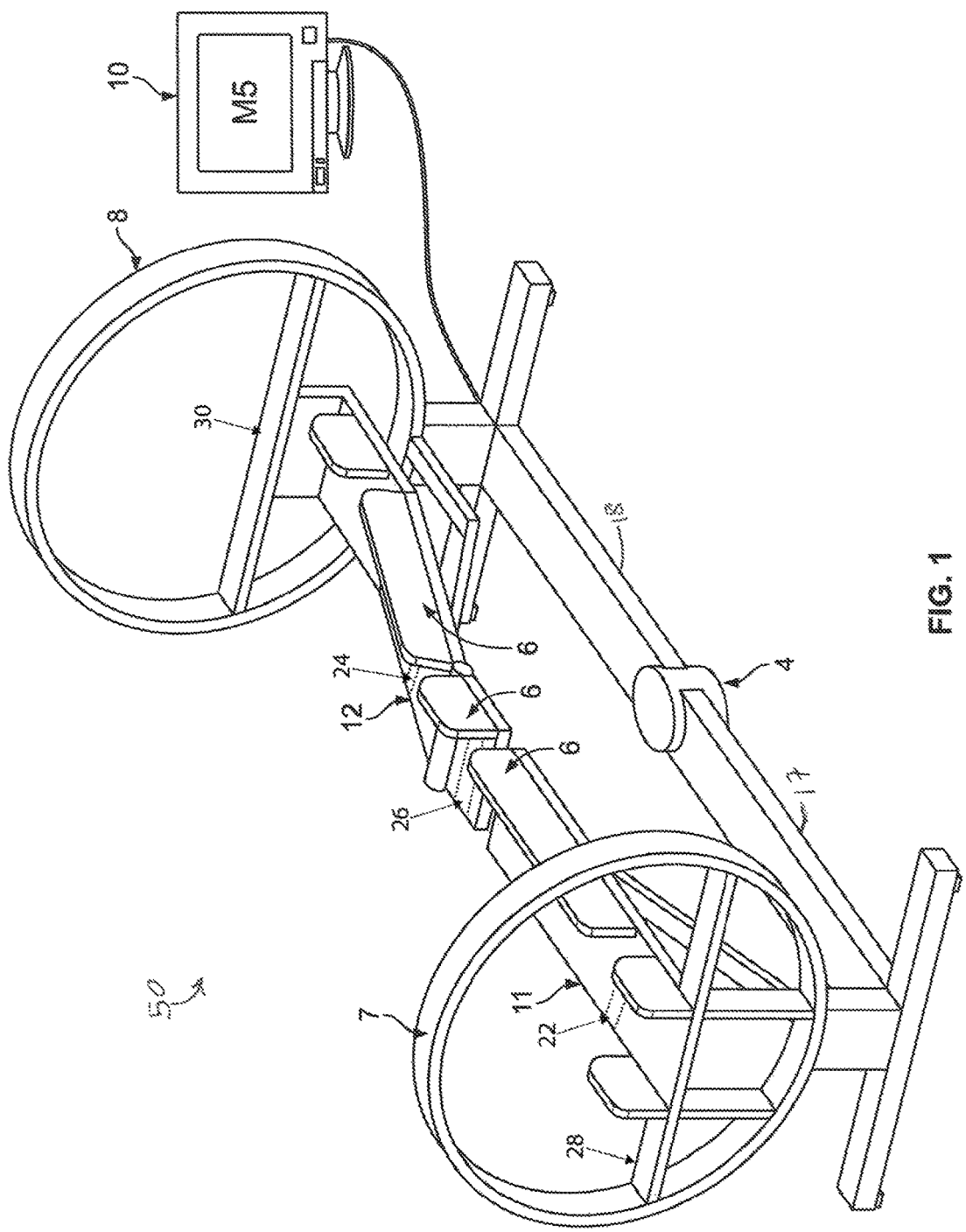
FIG. 1 shows a perspective view of a patient positioning system, according to an exemplary embodiment of the subject disclosure.

The following detailed description references specific embodiments of the subject disclosure and accompanying figures, including the respective best modes for carrying out each embodiment. It shall be understood that these illustrations are by way of example and not by way of limitation.

Illustrative embodiments of the subject matter are described below. In the interest of clarity, not all features of an actual implementation are described in this specification. It will of course be appreciated that in the development of any such actual embodiment, numerous implementation-specific decisions must be made to achieve the developers' specific goals, such as compliance with system-related and business-related constraints, which will vary from one implementation to another. Moreover, it will be appreciated that such a development effort might be complex and time-consuming, but would nevertheless be a routine undertaking for those of ordinary skill in the art having the benefit of this disclosure. The patient positioning systems and related methods disclosed herein boast a variety of novel features and components that warrant patent protection, both individually and in combination.

While the subject matter is susceptible to various modifications and alternative forms, specific embodiments thereof have been shown by way of example in the drawings and are herein described in detail. It should be understood, however, that the description herein of specific embodiments is not intended to limit the subject matter to the particular forms disclosed, but on the contrary, the subject matter is to cover all modifications, equivalents, and alternatives falling within the spirit and scope of the subject matter as defined herein. For example, any of the features of a particular example described herein may be used with any other example described herein without departing from the scope of the present subject matter.

Figure 2:
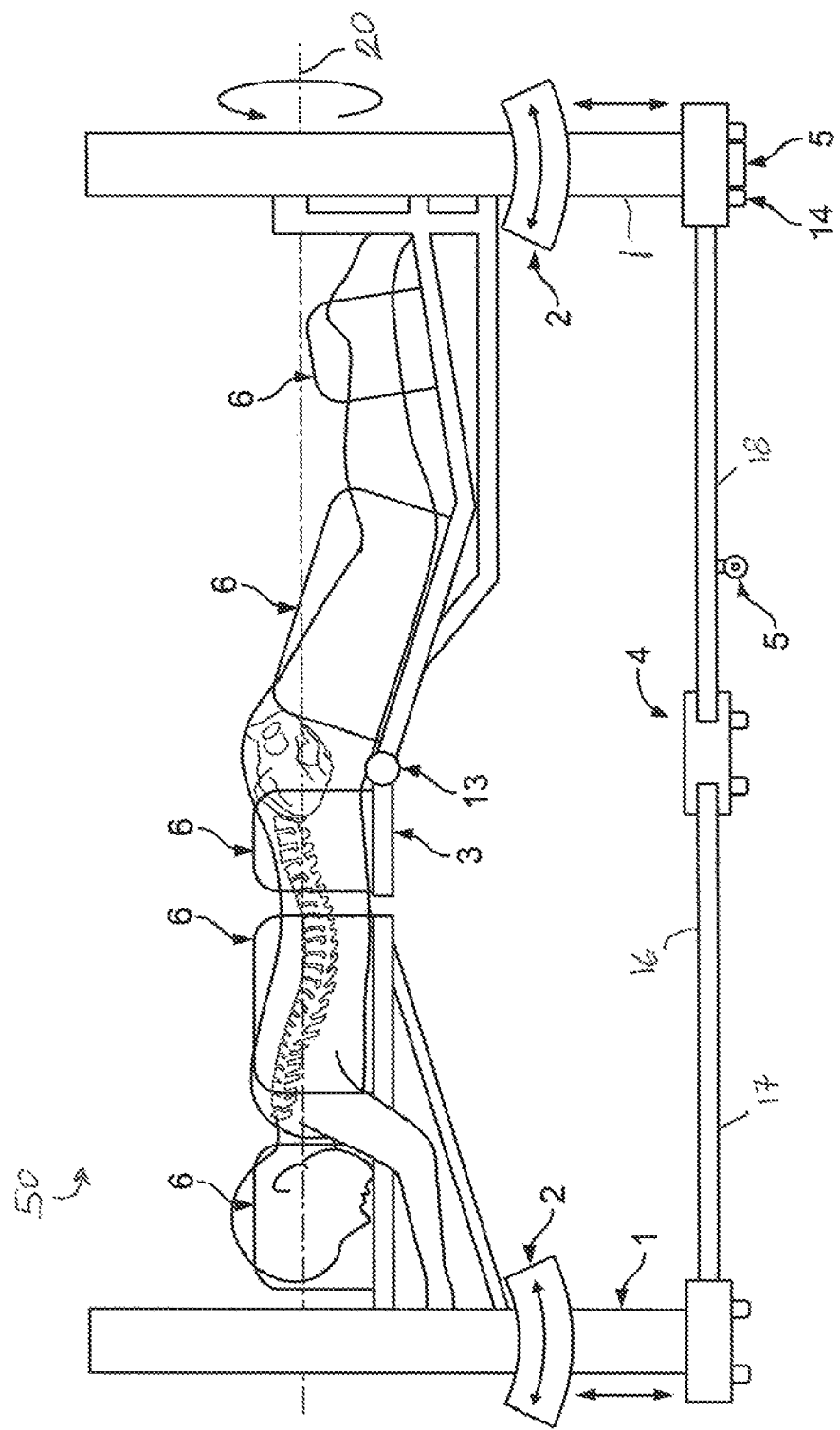
FIG. 2 shows a side view of a patient positioning system, according to an exemplary embodiment of the subject disclosure.

As will be described in greater detail below, there is provided an operating room (OR) table system 50 according to an example embodiment. FIG. 1-2 show the present system 50 is actually two independent tables 11 and 12, each with a corresponding end portion, which is shown as rings 7, 8, respectively. The two rings 7, 8 can be adjusted in height, synchronously or individually. A first crossing member 28 is attached to the interior portion of the ring 7. A second crossing member 30 is attached to the interior portion of the ring 8. A mechanism 2 is positioned in each of the vertical members 1 in the base 16 of the table which is connected to each ring 7, 8 allows for this height adjustment of the rings 7, 8, which in turn adjusts the height of the tables 11, 12 and the patient thereon. The base 16 is further separated into a superior base portion 17 and an inferior base portion 18, each of which moves independent of the other portion as will be described below. The movement of superior ring 7 and superior base portion 17 affect the positioning of table 11, and the movement of inferior ring 8 and superior base portion 18 affect the positioning of table 12.

The rings 7, 8 may be angled from vertical via a mechanism 2 between the vertical member 1 and the rings themselves 7, 8. This allows for inclination of the tables 11, 12 individually, allowing the spine to flex or extend when in the patient is positioned in the prone position. When the patient is rotated 90 degrees to the lateral decubitus position, this mechanism 2 acts as the break in the table, allowing the lateral bending of the spine in order facilitate an XLIF® or other lateral access spine procedure at the lower lumbar levels. As the inferior table 12 is not directly coupled to the superior table 11, with the addition of the pelvis being constrained to the inferior table 12, the patient's hips and/or pelvis region are opened up, allowing more complete access to the spine.

The tables 11, 12 may each be independently rotated 360 degrees. Mechanisms within the rings 7, 8 engage a feature on the frame of the table allowing for rotation of each table 11, 12 either synchronously or individually. The axis of rotation 20 of the rings 7, 8 should be aligned when the tables 11, 12 are rotated. This rotation allows for intra-operative repositioning of the patient, without having to remove them from the table system 50. The patient is securely strapped to the tables 11, 12 during rotation/repositioning. Additional accessories (not shown) provide constraints to hold the patient to the individual patient frames 6. The patient frames 6, which are shown as vertical boards in the exemplary embodiment, provide a surface for the patient to rest when in the lateral decubitus position. Similarly, additional posterior boards (not shown) may be attached to the main table to facilitate a supine position.

The inferior table 12 can also pivot relative to the superior table 11 via a pivoting mechanism 4 in the base cross member 16. The static feet 14 of the inferior table 12 can be lifted allowing the inferior base's roller wheels 5 to touch the floor. This provides a way for the surgeon to adjust the angle of the central sacral vertical line (CSVL) relative to the stationary head of the patient. This is an additional mechanism to control the positioning of the patient. The inferior base 18 may also translate left or right relative to the superior base 17 via pivoting mechanism 4. Thus, pivoting mechanisms allows both angular pivot and linear translation movement between superior base 17 and inferior base 18. This flexibility on position allows, for example, coronal alignment of the pelvis relative to the C7 vertebral level. By way of example, the angle of the CSVL may be measured and tracked, for example, using the systems and methods shown and described in Patent Application Number PCT/US2014/059974, entitled "Systems and Methods for Planning, Performing, and Assessing Spinal Correction During Surgery," filed Oct. 9, 2014, which is incorporated by reference herein in its entirety into this disclosure.

According to an example method, the patient is first positioned on the table in the prone position. The pelvis is supported by an adjustable table segment 3 of the inferior table 12, which is closest to the end of the superior table 11. The angle of this segment 3 is adjustable relative to the inferior table 12 segment supporting the legs via a hinge mechanism 13. This allows the pelvis to either retrovert or antevert depending on the desired pelvic position. Anteversion occurs when the segment 3 is rotated toward the floor. Anterversion of the pelvis would also effectively provide added lordosis to the lumbar spine by increasing the Sacral Slope. By way of example, the patient's sacral slope may be measured and tracked using the systems and methods described in the '974 application.

A center leaf section (not shown) of the table segment 3 could be removed to allow access for an anterior or anterolateral type of procedure (for example, ALIF) when the patient is positioned in the supine position.

All table articulations can be controlled from the computer control software 10. Moreover, position sensors at each articulation give positional feedback (height, angle, translation, force, pressure, etc.) to various software applications running on a neuromonitoring system (e.g. NVM5®) 10 in communication with the O.R. table. These applications could provide data to the surgeon regarding proper alignment or positioning of the patient. The neuromonitoring system that may be used in conjunction with the present subject matter may be, for example, that described in U.S. Pat. No. 8,255,045, entitled "Neurophysiologic Monitoring System," issued Aug. 28, 2012, which is incorporated herein in its entirety into this disclosure. The combination of the present subject disclosure along with the neuromonitoring systems, such as the one cited herein, allow for real time adjustment of various portions of a patient's body during a procedure based on changes in the neurophysiologic testing results. The present system 50 can then either automatically or manually adjust one or more segments of the O.R. bed in an effort to improve the neurophysiologic testing results (e.g., back to a baseline value).

The table system 50 is particularly useful when integrated with neurophysiologic monitoring system 10 such that intra-operative neurophysiologic monitoring may be used to ascertain the effect of patient positioning on the health and status of the nervous system. The system 50 is capable of integrating with a neurophysiologic monitoring system, e.g., the NuVasive) NVM5®, Cadwell Cascade, SafeOp Surgical positioning effect monitoring device. One exemplary technique involves using pre-operative and/or intra-operative data to reduce the incidence of ischemic effects of the upper extremity positioning, e.g., automatic repositioning of the patient's arms based Ulnar Nerve SSEPs. Another exemplary technique involves using pre-operative and/or intra-operative data to reduce the incidence of nerve irritation of one or more nerves in the lumbar plexus. Automatic reposition of table break will be done based on femoral nerve responses (e.g., transcutaneous nerve root responses). The patient module of a neurophysiologic monitoring system 10 could fit/plug into a dedicated receptacle in the table system 50, for example at the inferior base portion 18 of the table. This would allow for improved access in and around the OR floor underneath the table.

The table system 50 integrates with a computer assisted surgery system, e.g., the NuVasive® NVM5® system, the StealthStation, etc. In one exemplary technique, it uses pre-operative and/or intra-operative data to physically rotate and/or translate the patient in order to facilitate the placement of interbody implants and/or supplemental fixation (e.g., rods, lateral plates, etc.).

Force or pressure sensors 26 embedded within table segment 3 provide feedback to the neurophysiologic monitoring system or computer-assisted surgery (e.g. NVM5®) software application 10 as to current or constant force applied to the surface of that segment 3 from the pelvic spine. This information can potentially be used to understand the "stiffness" of the spine, or if the surgeon has performed enough posterior releases of the anatomy in order for the pelvis to freely antevert onto the adjusted table segment 3. If the force is constant when the segment 3 is rotated toward the floor, then the pelvis/spine is flexible. If the force diminishes when the segment 3 is rotated, then the spine is stiff and more releases must be done. The targeted rotation of the pelvis would be based on the planned Sacral Slope of the spine, measured intra-operatively using intra-operative anatomical measuring software (e.g., NuvaMap™ O.R. software) 10, for example using the systems and methods disclosed in the '974 application.

Data feedback of the individual superior 11 or inferior 12 tables with respect to relative height using embedded sensors 22 and 24, allow for an application in the NVM5® 10 to position the patient so that the patient is in a preferred sagittal alignment (e.g., SVA, +1-5 cm). This table data would work in conjunction with spatial anatomical data acquired from digitizing specific patient anatomy as disclosed in the '974 application.

As may be appreciated by one having ordinary skill in the art after considering the present disclosure, there are numerous benefits and capabilities of the 360 Degree Rotating Table system 50. One of the benefits is the overall configuration of the table system 50 which allows for versatility with respect to other operating room equipment. For example, there is a plenty of room for a C-arm x-ray machine under the table. The C-arm x-ray may be positioned underneath or around the table such that the patient is perfectly positioned in with the middle of the C arm. Further, any patient connected wires, hoses, intravascular (IV) lines, etc., can exit the rings 7, 8 either superiorly or inferiorly, respectively. When the tables 11, 12 are rotated, those wire, tube and conduit connections (not shown) do not need to be repositioned. They just rotate with the tables 11, 12. This versatility also allows an anesthesiologist to have full access to the patient's head or upper body region through ring 7 to administer anesthetic agents, maintain the airway, etc., as needed without intruding into the space where the surgical operation is taking place. This design has the added benefit of allowing higher visibility access to the patient's airway thereby improving patient safety. The table system 50 may further possess static maintenance/stabilization features that protect critical patient attachments during rotation and provide confidence that none of the items will pull out, e.g., endotracheal tube, urinary catheter, EKG leads, IV lines, neurophysiologic monitoring leads.

In some embodiments, one or more drapes may be attached to the table rings 7, 8 and wrapped circumferentially around the patient. The tables 11, 12 can be rotated 360 degrees without having to re-drape.

The versatility in movement and rotation for table system 50 comes from a number of unique features and capabilities. For example, the tables 11, 12 are capable of moving up/down, moving side-to-side (rotating laterally), and tilting the head of the table down (Trendelenburg position) and up (Reverse Trendelenburg position). This ability allows many positions, which include prone, lateral, and supine table rotation functionality to support a triple position surgery method (e.g., an ALIF at one or more spinal levels, an XLIF® at one or more spinal levels, and a PLIF or TLIF at one or more spinal levels). The table may include capability to break at the trochanter which is a requirement for XLIF® and other lateral access spine surgeries with fine-tuned control (manual and/or motor) of the amount of break when rotating between positions (e.g., between lateral and prone positions). The joints and mechanisms for such movement and motion have not been shown but would be apparent to one having ordinary skill in the art after consideration of the present disclosure.

The table system 50 provides many different patient positioning features. The table may possess default table settings based on user profile, surgical procedure, or the like. The table system 50 has the ability to automatically position to default table settings based on user selection. It further allows for arms, legs, hips, stomach, etc. to be selectively positioned for desired stability depending on patient position (prone, supine, lateral decubitus). This may occur by being positioned on moveable and/or retractable bolsters, air bladder, or the like (not shown). Further, the present system provides the ability for holding hips/stomach in a position to keep stomach in contralateral position (belly forward) which is a strong preference in an XLIF® or other lateral access spine procedures.

The table system 50 may further include modular support components that may be provided to accommodate necessary support for weight-bearing body parts in each of the lateral decubitus, prone, and supine positions. In the prone position, support components (such as patient frames 6) may allow for the ability to create lordosis with body weight. In the prone position, support components may allow for the ability to create lordosis focally/segmentally which allows for targeted correction at each level of the patient's spine. The table may be provided with an adjustable roller bar or air bladder that acts as a fulcrum to induce lordosis or reduce deformity at each spinal segment. The roller bar or air bladder may be radiolucent (plastic or plastic composite (e.g. CFRP)). The roller bar or air bladder may be "hands-free", i.e., ideally it would not require an OR attendee to hold it in place and could be driven by foot pedal motors. This would help surgical flow as the surgeon moves operations from level to level. The mechanism would work most easily when the patient is positioned in lateral since the operating corridor is 90 degrees to the plane that the roller bar or air bladder is working in (but is not limited to lateral—for example, in the prone position, windows/apertures may be added to gain access through to the spine through the mechanism). The system 50 in conjunction with control software 10 allows for dial in measurements or positions of various body regions for ideal positioning of specific patient based on anatomical or surgical considerations (manual or motor control). Further ability allows for independent articulating left and right arm positions—up/down; sideslide; within full range of motion of shoulder, elbow, and wrist joint. Other exemplary embodiments allow for independent articulating left and right leg positions—up/down; sideslide; within full range of motion of hip, knee, and ankle joint. This may be done by duplication the number of superior 11 and inferior 12 tables and having a patient rest on all tables. Each such table would have more fine control of a different portion or appendage of the patient. Single prep surgery may be conducted in that a patient may be flipped 90, 180, 270, 360 degrees without having to break scrub.

The table may be constructed from various components as described herein. It may be constructed of a radiolucent material, e.g., carbon fiber or similar material known in the art, and may be sized and dimensioned to allow radiological equipment (e.g., C-arm, O-arm, BodyTom®) to pass under, around, over the table. The table system 50 is sized and dimensioned to safely accommodate patients of all shapes and sizes. Spine surgery is only one type of surgery that this table could accommodate, but any type of surgical procedure where patient positioning is an important consideration would be relevant to this table system 50. Further enhancements may include adapter features that couple to a preoperative table that facilitate patient positioning onto OR table. These can be a universal adapter or table-specific adapter. The present table system 50 is constructed so that it can accommodate a 2 position surgery (e.g., lateral-decubitus and prone) and/or a 3 position surgery (e.g., lateral-decubitus, prone, supine), and maintain sterility of the table and the patient when rotating to all three positions.

As discussed above, the table may be integrated with a C-arm and intraoperative fluoroscopic workflow. The table system 50 is in communication with the C-arm and may possess bookmarking capabilities that capture the exact Trendelenberg/tilt/height of the table when a C-arm shot was taken so that the user can take a shot with desired anatomical features of a particular surgical procedure (e.g., "crisp" endplates, spinous process). This allows the C-arm to be moved out of the way, the table to be moved, etc. and the table to be moved to the same exact orientation as it was when the fluoroscopic image was taken so the surgeon/C-arm technician knows that the same or similar quality C-arm shot is obtainable quickly. The table system 50 may be used to perform micromotion in all planes on the table so the X-ray technician doesn't have to do this. The C-arm could be used for gross maneuvers and target the general vicinity of the ideal C-arm shot. The table could perform the finer maneuvers so the X-ray does not have to do it with the bulky C-arm. In this way, the table could take the place of the C-arm technician after the initial gross maneuver, freeing that person to go on to other patient care duties.

The foregoing disclosure of the exemplary embodiments of the present subject disclosure has been presented for purposes of illustration and description. It is not intended to be exhaustive or to limit the subject disclosure to the precise forms disclosed. Many variations and modifications of the embodiments described herein will be apparent to one of ordinary skill in the art in light of the above disclosure. The scope of the subject disclosure is to be defined only by the claims appended hereto, and by their equivalents.

Further, in describing representative embodiments of the present subject disclosure, the specification may have presented the method and/or process of the present subject disclosure as a particular sequence of steps. However, to the extent that the method or process does not rely on the particular order of steps set forth herein, the method or process should not be limited to the particular sequence of steps described. As one of ordinary skill in the art would appreciate, other sequences of steps may be possible. Therefore, the particular order of the steps set forth in the specification should not be construed as limitations on the claims. In addition, the claims directed to the method and/or process of the present subject disclosure should not be limited to the performance of their steps in the order written, and one skilled in the art can readily appreciate that the sequences may be varied and still remain within the spirit and scope of the present subject disclosure.

What is claimed is:

1. A system for maintaining a patient in a desired position, the system comprising:
   a first end member having an open interior portion, and a first crossing member attached to the interior portion of the first end member;
   a second end member having an open interior portion, and a second crossing member attached to the interior portion of the second end member;
   a base connecting the first and second end members, wherein the base includes a joint portion which divides the base into a first base portion which connects to the first end member and a second base portion which connects to the second end member;
   a first substantially flat platform connected to the first crossing member;
   a second substantially flat platform connected to the second crossing member;
   wherein the joint, portion allows a pivoting motion between the first base portion and the second base portion such that the first and second platforms are independently movable along a vertical axis, wherein movement along the vertical axis enables the first and second platforms to be arranged in or out of a parallel alignment.

2. The system of claim 1, wherein the first and second end members are circular.

3. The system of claim 2, wherein the first crossing member is a chord attached to the interior portion of the first end member, wherein the second crossing member is a chord attached to the interior portion of the second end member.

4. The system of claim 1, wherein the first end member has a first center and rotates completely around the first center, wherein the second end member has a second center and rotates completely around the second center.

5. The system of claim 4, wherein each of the first and second end members rotates independently of the other end member.

6. The system of claim 1, wherein each of the first and second end members can tilt independently with respect to each other.

7. The system of claim 1, wherein each of the first and second end members independently moves in a vertical direction with respect to the base.

8. The system of claim 1, further comprising a patient frame positioned perpendicular to the first platform.

9. The system of claim 1, further comprising a patient frame positioned perpendicular to the second platform.

10. The system of claim 1, wherein the second platform is connected to a distal platform at an end opposite to where it connects to the second crossing member.

11. The system of claim 10, wherein the connection between the second platform and the distal portion is a pivot.

12. The system of claim 10, wherein the distal platform further comprises a patient frame positioned perpendicular to the distal platform.

13. The system of claim 1, further comprising a position monitoring system in communication with the first and second platforms.

14. The system of claim 13, further comprising sensors in each of the first and second platforms which are adapted to take readings from a patient in contact thereon, and transmit the readings to the position monitoring system.

15. The system of claim 14, wherein the position monitoring system is adapted to transmit signals to change from a first to a second position of the first and second platforms with respect to the patient.

16. A system for maintaining a patient in a desired position, the system comprising:
   a first end member having an open interior portion, and a first crossing member attached to the interior portion of the first end member;
   a second end member having an open interior portion, and a second crossing member attached to the interior portion of the second end member;
   a base connecting the first and second end members, wherein the base includes a joint portion which divides the base into a first base portion which connects to the first end member and a second base portion which connects to the second end member;
   a first substantially flat platform connected to the first crossing member;
   a second substantially flat platform connected to the second crossing member; sensors within the first and second platforms adapted to read signals thereon and generate signals; and
   a position monitoring system adapted to receive the signals from the sensors and determine a physiological condition of the patient;
   wherein the joint portion allows a pivoting, motion between the first base portion, and the second base portion such that the first and second platforms are independently movable along a vertical axis, wherein movement along the vertical axis enables the first and second platforms to be arranged in or out of a parallel alignment.

* * * * *